United States Patent [19]

Gogolewski et al.

[11] Patent Number: 4,661,530

[45] Date of Patent: Apr. 28, 1987

[54] BIOCOMPATIBLE, ANTITHROMBOGENIC MATERIALS SUITABLE FOR RECONSTRUCTIVE SURGERY

[75] Inventors: Sylwester Gogolewski, Renens, Switzerland; Albert J. Pennings, Norg, Netherlands

[73] Assignee: Medtronic, Inc., Minneapolis, Minn.

[21] Appl. No.: 597,160

[22] PCT Filed: Jul. 15, 1983

[86] PCT No.: PCT/NL83/00027

§ 371 Date: Mar. 13, 1984

§ 102(e) Date: Mar. 13, 1984

[87] PCT Pub. No.: WO84/00302

PCT Pub. Date: Feb. 2, 1984

[30] Foreign Application Priority Data

Jul. 16, 1982 [NL] Netherlands .......................... 8202893

[51] Int. Cl.$^4$ ....................... C08G 18/14; C08G 18/34
[52] U.S. Cl. ..................................... 521/137; 521/62; 521/63; 521/905; 521/916
[58] Field of Search ................. 521/137, 905, 916, 62, 521/63

[56] References Cited

U.S. PATENT DOCUMENTS

| | | | |
|---|---|---|---|
| 3,896,802 | 7/1975 | Williams | 128/149 |
| 3,975,350 | 8/1976 | Hudgin et al. | 521/63 |
| 4,049,592 | 9/1977 | Marans et al. | 521/916 |
| 4,132,839 | 1/1979 | Marans et al. | 521/916 |
| 4,173,689 | 11/1979 | Lyman et al. | 521/64 |

OTHER PUBLICATIONS

Coury et al., Reprint from "Advances in Urethane Science & Technology," vol. 9, pp. 130–168 (1984).
"Biologic and Synthetic Vascular Prostheses", edited by J. C. Stanley, M.D., published by Grune & Stratton, 1982.
"Structural Order and Blood Compatibility of Polymeric Prosthesis", IUPAC Macromolecular Symposium, Ciardelli, C. F. & Giusti, P. Eds. Pergammon Press, Ltd., Oxford, 1980.
"An Elastomeric Vascular Prostheses", vol. XXIV Trans. Am. Soc. Artif. Intern. Organs, 1978, p. 209.
"Blood-Materials Interactions—20 Years of Frustration"; vol. XXVII, by Andrade et al., Trans. Am. Soc. Artif. Intern. Organs, 1981, p. 659.
"Experimental Study of the New Synthetic Vascular Graft" by Gruss et al., J. Cardiovas. Surg., 22, 1981 at page 518 of the XV World Congress of the International Cardiovascular Society.
"Biodegradable Materials of Poly(L-Lactic Acid): 1. Melt-Spun and Solution-Spun Fibres", by B. Eling, S. Gogolewski and A. J. Pennings, Polymers, 1982, vol. 23, Oct., pp. 1587–1593.
"Infrared Studies of Segmented Polyurethane Elastomers. I. Hydrogen Bonding", by R. W. Seymour, G. M. Estes and S. L. Cooper, Reprinted from Macromolecules, vol. 3, pp. 579–583, Sep.-Oct. 1970.
"Infrared Studies of Segmented Polyurethane Elastomers. II. Infrared Dichroism", by G. M. Estes, R. W. Seymour and S. L. Cooper, reprinted from Macromolecules, vol. 4, pp. 452–457, Jul.-Aug. 1971.
"Thermoplastic Polyurethane Elastomer Molecular Weight-Property Relations, Further Studies", by C. S. Schollengberger and K. Dinbergs, Advances in Urethane Science and Technology, vol. 7, 1979, pp. 1–34.
"Study of the Degradation of Polyurethanes. II. ESR Study on the Photodecomposition of Polyurethanes and Ethylphenylcarbamate", Polymer Letters Edition, vol. 13, pp. 535–542 (1975).
"Life Support Systems", The Journal of the European Society for Artificial Organs, Proceedings XI Annual Meeting ESAO, Alpbach-Innsbruck, Austria, Sep. 1984, vol. 2, Supplement 1.
"Biodegradable Materials of Polylactides, 4$^a$)—Porous Biomedical Materials Based on Mixtures of Polylactides and Polyurethanes", by S. Gogolewski and A. J. Pennings, Makromol. Chem. Rapid Commun. 3, 839–845 (1982).
"Artificial Organs", Fourth Congress of the International Society for Artificial Organs, vol. 7, Abstracts, Nov. 14–17, 1983.
"Growth of a Neo-Artery Induced by a Biodegradable Polymeric Vascular Prosthesis", by S. Gogolewski and A. J. Pennings, Makromol. Chem. Rapid Commun., 4, 213–219 (1983).
Macro '83 Bucharest-Romania, Sep. 5–9, 1983, 3rd Circular, "Porous Polylactide Materials for Medical Application", by S. Gogolewski and A. J. Pennings.
Paper entitled "Gronigen Biodegradable Vascular Prosthesis", by S. Gogolewski and A. J. Pennings.
"Resorbable Materials of Poly (L-lactide). II. Fibers Spun from Solutions of Poly(L-lactide) in Good Solvents", by S. Gogolewski and A. J. Pennings, Journal of Applied Polymer Science, vol. 28, 1045–1061 (1983).
Reprint from Polymer, "General Crystallization Behaviour of Poly (L-lactic acid) PLLA: 2, Eutectic Crystallization of PLLA" by R. J. M. Zwlers, S. Gogolewski and A. J. Pennings.
"Development of a Neo-Artery Induced by a Biodegradable Polymeric Vascular Prosthesis", by E. Lommen et al., Trans. Am. Soc. Artif. Intern. Organs, vol. XXIX, 1983, pp. 255–259.
"Microporous, Compliant and Biodegrable Vascular Prostheses", 4th Congress—Intl. Soc. for Artificial Organs, Nov. 14–17, 1983, vol. 7, Abstracts.

Primary Examiner—Herbert S. Cockeram
Attorney, Agent, or Firm—Vidas & Arrett

[57] ABSTRACT

Biocompatible, highly antithrombogenic material for reconstructive surgery, which is based on poly (L-lactic acid) and or poly (dL-lactic acid) and segmented polyester and urethanes or polyether urethanes.

6 Claims, No Drawings

BIOCOMPATIBLE, ANTITHROMBOGENIC MATERIALS SUITABLE FOR RECONSTRUCTIVE SURGERY

The invention relates to a new biocompatible, highly antithrombogenic material, of adjustable porosity, compliance and biodegradability, based on polylactic acid and segmented polyurethanes, for reconstructive surgery, which can be built up in layers with different compositions and characteristics and can be modelled in various shapes by including reinforcement material. The versatility of the material according to the present invention gives it a unique adaptability to the biological tissue in which it is incorporated, so that the synthetic material is built up into a new functional entity in reconstructive surgery.

Most synthetic materials used for reconstruction do not have the same mechanical proporties as the specific biological tissue and so do not match its specific function. It is known that the specific function of tissue is the trigger of the constant rebuilding of tissue in the growth during life. The variability of the elastic properties of the material according to the present invention renders it possible to match the mechanical properties of most of the biological tissue that has to be replaced in the body.

As its porosity can be varied, the ingrowth and overgrowth of tissue for complete incorporation can be regulated to provide optimum conditions for a specific replacement. Its adjustable biodegradability makes it possible, if desired, to have the synthetic material completely replaced by biological tissue.

Because of the possibility to produce the material in layers of different compositions, it is also possible to have the characteristics of each layer match the function of the biological tissue needed to rebuild that layer.

Because the material can be modelled by the shapes of mandrels by a dipping technique, every form can be produced to match the shape of an organ to be replaced, such as a tubular neo-artery for example. But also a more complex organ such as a trachea can be produced from this synthetic material, including a reinforcement material in the layers to maintain its shape during the alternating positive and negative pressures occurring in the trachea and to prevent collapsing. The constructive reinforcement material can be made of a different material, for example porous hydroxy apatite, which could induce bone formation.

Due to the biodegradability and high flexibility of the polylactide-polyurethane porous membranes, these materials can also be used to cover satisfactorily large experimental full-thickness skin wounds. Such membranes can effectively protect these wounds from infection and fluid loss for a long time.

Thus these combinations give a wide range of new possibilities in reconstructive surgery, all based on the same principle that perfect matching of the mechanical properties of biological tissue and synthetic materials creates one functional unity between biological tissue and the synthetic material which allows complete incorporation and rebuilding to a new organ. This new composition has been tested in animal experiments, primarily with rabbits, as vascular and tracheal prostheses and artificial skin. In these experiments true biocompatibility and a high degree of antithrombogenicity of the material was demonstrated. The experiments with the trachel prosthesis revealed that quick tissue ingrowth from the peritracheal tissue is induced if relatively large pores (100$\mu$) were used on the outside. However, overgrowth of tissue on the luminal side needed only a thin connective tissue layer to which epithelium became firmly attached and differentiated. This was achieved with relatively small pores on the inside (10–20$\mu$). Between the layers of various pore sizes a reinforcement of a spiral bead may be embedded.

This possibility of variation by means of different layers can also be used for the composition of an artificial skin where such functions as controlled evaporation, ingrowth of tissue, seeding of epithelial cells and resistance to outside micro-organism require layers with different characteristics.

More specifically the invention relates to the provision of a material which comprises the following composition in wt. %: poly(L-lactic acid) and/or poly(dL-lactic acid) with a viscosity-average molecular weight in the range of $2\times 10^5$ to $5\times 10^6$, from 5 to 95; and polyester urethane or polyether urethane, from 5 to 95. Polyester urethane or polyether urethane may be based on: polytetramethylene adipate, poly(ethyleneglycol adipate), poly(tetramethylene oxide), poly(tetramethylene glycol) or poly(diethyleneglycol adipate, p,p'-diphenylmethane diisocyanate, or toluene diisocyanate, or hexamethylene diisocyanate and 1,4 butanediol or ethylene diamine.

The segmented polyurethane imparts the desired flexibility, strength and antithrombogenity to the material.

The polylactic acid ensures the required modulus and porosity. By varying the proportion of polylactic acid, the proposed compliance and type or porosity can be controlled. As the ester, ether and urethane groups of polyurethane and the carboxylic group of polylactic acid exhibit poor hydrolytic stability, the material easily breaks down to be eliminated from the body after replacement of the graft by the body tissues.

In order to increase the rate of material resorption in the body, it is recommended to use a material which contains at least 20% by weight of polylactic acid and polyester urethane, based on hexamethylene diisocyanate, polyethyleneglycol adipate and 1,4-butanediol.

In order to improve antithrombogenic effect, the polyurethane based on polytetramethylene glycol and p,p'-diphenylmethane may be used.

For the preparation of arteries, arteriovenous shunts or cardiopulmonary bypass, the following compositions of the material, in % by weight, are recommended:
a. poly(L-lactic acid) or poly(dL-lactic acid), 20; polyether urethane, 80.
b. polylactic acid, 30; polyether urethane, 70.
c. polylactic acid, 15; polyether urethane, 85.

For the preparation of veins with a diameter in the range of 1,5 to 10 mm, the following composition, in % by weight, is recommended:
a. polylactic acid, 80; polyester urethane, 20.
b. polylactic acid, 70; polyester urethane, 30.
c. polylactic acid, 60; polyester urethane, 40.

For the preparation of tracheal prostheses with a diameter in the range of 7–25 mm, the following composition, in % by weight, is recommended:
a. polylactic acid, 50; polyester or polyeter urethane, 50.
b. polylactic acid, 40; polyester or polyeter urethane, 60.

For the preparation of artificial skin having a size in the range of 50 to 500 mm by 50 to 500 mm the following composition, in % by weight, is recommended:

polylactic acid, 20 to 50;
polyester urethane 50 to 80.

The techniques applied for the preparation of tubular grafts and porous membranes may for example be as follows:

A. Vascular grafts (a) For higher concentrations of polylactic acid in the mixture: Polylactic acid is dissolved in chloroform at room temperature and 5 to 20% by weight of sodium citrate in chloroform ethanol mixture is added to the solution. Polyurethane is dissolved in tetrahydrofuran so as to give a solution with a concentration in the range of 5-14% by weight.

The solutions of polylactic acid and polyurethane are mixed together right before the preparation of the tubes.

The tubes are prepared on a stainless steel mandrel coated with polytetrafluoroethylene. For this purpose the mandrels are dipped into the polymer solution and dried at room temperature. Dipping and solvent evaporation procedure is repeated to provide the graft with a required wall thickness. The grafts are extracted with distilled water and ethanol for 5 to 10 hours to remove sodium citrate.

Depending on the concentration of sodium citrate in the polymer solution and the proportion of polylactic acid, the size of the pores formed in the grafts is in the range of 5 to 200 μm. In addition the pore size may be adjusted by changing the polymer concentration in the solution from which the grafts are made. From a more concentrated solution grafts with smaller pores are obtained. When layers of polymer are deposited on the mandrel from solutions with different polymer concentrations composite grafts are formed having a gradually increasing pore size, suitable for certain types of implants.

(b) For higher concentrations of polyurethane in the mixture: Polylactic acid is dissolved in tetrahydrofuran at 50° to 90° C. Polyurethane is dissolved separately in tetrahydrofuran. The two solutions are mixed together prior to the graft preparation. The concentration of polymer in the solution is in the range of 5-20% by weight.

Tubes are prepared on stainless steel mandrels coated with polytetrafluoroethylene (PTFE), the mandrels being dipped into the polymer solution maintained at a temperature of 60° to 85° C. and next into an ethanol distilled water mixture to precipitate the polymer.

Depending on the concentration of polymer in the solution, a porous structure with different pore size is formed. The structure is composed of thin, elastic polyurethane fibers covered with a thin layer of polylactic acid.

As a general rule it is recommended that more concentrated polymer solutions are used for the preparation of grafts having smaller pore sizes.

These highly porous polylactic acid-polyurethane materials composed of randomly distributed holes and elastic fibers exhibit both radial and linear compliance.

In all cases the pore-to-matrix ratio by volume can be adjusted from 0 to 90 percent.

B. Tracheal Prostheses

Solutions of polymers were prepared as described in Aa and Ab.

After the deposition of 2 to 3 polymer layers on the mandrel, a reinforcing bead extruded from polyether urethane or polyamide urethane is wound tightly around the polymer-coated mandrel and another coating of polymer is applied. Due to partial dissolution and swelling of the surface of the reinforcing bead, an excellent, homogenous connection between the bead and the inner and outer walls of the prostheses is formed.

C. Artificial skin

Solutions of polymers are prepared as described in Aa and Ab. A glass cylinder with a rough, sand-blasted surface is dipped into the polymer solution maintained at a temperature of 60° to 85° C., and next into an ethanol distilled water mixture to precipitate the polymer.

After washing with water and extraction with ethanol the porous sleeve is removed from the glass mould and cut along its longitudinal axis.

On the upper side of the membrane a polyether urethane or Dow Corning Silastic Medical Adhesive Type A is spread.

The diameter and the length of the glass mold may be in the range of 50 to 200 mm and 50 to 200 mm, respectively, depending on the size of the piece of artificial skin required for implantation.

The proposed material in the form of vascular and tracheal grafts and porous membranes-artificio with various polylactic acidpolyurethane compositions and porosities, was tested in vivo for anticlotting properties and tissue ingrowth by implanting into chincilla rabbits and albino rats weighing 2 to 2.5 kg and 100 to 150 g, respectively.

Histological analysis showed no clotting, connective tissue ingrowth, blood vessels ingrowth, etc.

What is claimed:

1. Biocompatible, porous, highly antithrombogenic material for reconstructive surgery, which is prepared from mixtures of poly(L-lactic acid) and/or poly(dL-lactic acid) and segmented polyester urethanes or segmented polyether urethanes.

2. Material according to claim 1, characterized by the following composition in % by weight:
poly(L-lactic acid), 5 to 95, or
poly(dL-lactic acid), 5 to 95, and
polyester urethane, 5 to 95, or
polyether urethane, 5 to 95.

3. Material according to claim 1, characterized in that the polyester urethane is the reaction product of:
poly(tetramethylene adipate) or poly(ethyleneglycol adipate) reacted with p,p'-diphenylmethane diisocyanate, toluene diisocyanate or hexamethylene diisocyanate, and 1,4-butanediol or ethylene diamine; and the polyether urethane is the reaction product of:
poly(tetramethylene oxide), poly(tetramethylene glycol) or poly(diethyleneglycol adipate) reacted with p,p'-diphenylmethane diisocyanate, toluene diisocyanate or hexamethylene diisocyanate, and 1,4-butanediol, or ethylene diamine.

4. Biocompatible, porous, highly antithrombogenic, biodegradable articles prepared from mixtures of polylactic acid and segmented polyurethanes, wherein compliance is a function of the ratio between the polylactic acid and the polyurethane in the mixture.

5. Biocompatible, porous, highly antithrombogenic, biodegradable articles prepared from mixtures of polylactic acid and segmented polyurethanes, wherein the pore size is from 5 to 200 μm and the pore-to-matrix ratio is between 0 and 90 percent.

6. Material according to claim 2, characterized in that the polyester urethane is the reaction product of: poly(tetramethylene adipate) or poly(ethyleneglycol adipate) reacted with p,p'-diphenylmethane diisocyanate, toluene diisocyanate or hexamethylene diisocyanate, and 1,4-butanediol or ethylene diamine; and the polyether urethane is the reaction product of: poly(tetramethylene oxide), poly(tetramethylene glycol) or poly(diethyleneglycol adipate) reacted with p,p'-diphenylmethane diisocyanate, toluene diisocyanate or hexamethylene diisocyanate, and 1,4-butanediol, or ethylene diamine.

* * * * *

UNITED STATES PATENT AND TRADEMARK OFFICE
CERTIFICATE OF CORRECTION

PATENT NO. : 4,661,530
DATED : April 28, 1987
INVENTOR(S) : Gogolewski et al

It is certified that error appears in the above-identified patent and that said Letters Patent is hereby corrected as shown below:

Column 3, line 13, the numerals appearing as "5-14%" should read --5-15%--.

Signed and Sealed this

Twentieth Day of October, 1987

Attest:

DONALD J. QUIGG

Attesting Officer

Commissioner of Patents and Trademarks

UNITED STATES PATENT AND TRADEMARK OFFICE
CERTIFICATE OF CORRECTION

PATENT NO.  : 4,661,530
DATED       : April 28, 1987
INVENTOR(S) : Sylwester Gogolewski It is certified that error appears in the above-identified patent and that said Letters Patent are hereby corrected as shown below:

On the Title Page, Item [73] Assignee should read:

-- Rijksuniversiteit TE Groningen Broerstraat, The Netherlands --.

Signed and Sealed this

Fourteenth Day of June, 1988

*Attest:*

DONALD J. QUIGG

*Attesting Officer*      *Commissioner of Patents and Trademarks*

UNITED STATES PATENT AND TRADEMARK OFFICE
CERTIFICATE OF CORRECTION

PATENT NO.   : 4,661,530

DATED        : April 28, 1987

INVENTOR(S)  : Sylwester Gogolewski, et. al.

It is certified that error appears in the above-identified patent and that said Letters Patent is hereby corrected as shown below:

On the Title page

Item [73], Assignee:  should read -- RIJKSUNIVERSITEIT TE GRONINGEN, Groningen, The Netherlands.

Signed and Sealed this

Twenty-sixth Day of January, 1993

Attest:

STEPHEN G. KUNIN

*Attesting Officer*          Acting Commissioner of Patents and Trademarks